United States Patent
Roufs et al.

(10) Patent No.: US 6,967,206 B2
(45) Date of Patent: Nov. 22, 2005

(54) COMPOSITIONS AND METHODS FOR INCREASING GROWTH HORMONE LEVELS

(75) Inventors: James B. Roufs, San Monica, CA (US); Marc Lemay, Long Beach, CA (US)

(73) Assignee: Access Business Group International LLC, Ada, MI (US)

( * ) Notice: Subject to any disclaimer, the term of this patent is extended or adjusted under 35 U.S.C. 154(b) by 225 days.

(21) Appl. No.: 10/310,576

(22) Filed: Dec. 5, 2002

(65) Prior Publication Data

US 2004/0110783 A1 Jun. 10, 2004

(51) Int. Cl.⁷ .................. A61K 31/44; A61K 31/195
(52) U.S. Cl. ........................... 514/299; 514/561
(58) Field of Search ........................ 514/299, 561

(56) References Cited

U.S. PATENT DOCUMENTS

| | | | |
|---|---|---|---|
| 4,929,731 A | 5/1990 | Kozikowski et al. | |
| 5,104,880 A | 4/1992 | Kozikowski | |
| 5,106,979 A | 4/1992 | Kozikowski et al. | |
| 6,346,264 B1 * | 2/2002 | White | 424/439 |
| 6,461,634 B1 | 10/2002 | Marshall | |
| 6,521,266 B1 * | 2/2003 | Mann | 424/725 |

OTHER PUBLICATIONS

Young PW, Bicknell RJ, Schofield JG. "Acetylcholine stimulates growth hormone secretion, phosphatidyl inositol labelling, 45Ca2+ efflux and cyclic GMP accumulation in bovine anterior pituitary glands"; J Endocrinol Feb. 1979;80(2):203–13,[PMID:220365 Medline].

* cited by examiner

Primary Examiner—San-Ming Hui
(74) Attorney, Agent, or Firm—Alticor Inc.

(57) ABSTRACT

A composition for increasing GH levels in a mammal including effective amounts of huperzine A and secretagogue amino acids and methods thereof.

4 Claims, 2 Drawing Sheets

COMPOSITIONS AND METHODS FOR INCREASING GROWTH HORMONE LEVELS

FIELD OF THE INVENTION

The present invention relates to compositions containing an acetylcholinesterase inhibitor and secretagogue amino acids for increasing GH levels and methods thereof. In particular, the present invention is directed to compositions containing effective amounts of huperzine A and secretagogue amino acids for increasing growth hormone levels in a mammal.

BACKGROUND OF THE INVENTION

There is an ongoing interest in regulating growth hormone ("GH") because of its link to age-associated diseases. More specifically, GH is known to play a significant role in growth of all tissues, cell repair and regeneration, brain and organ function, sexual function, bone strength, energy, and metabolism. As individuals age, GH decreases and, as such, tissue repair and regeneration activity decreases. Amongst other age-associated diseases, a decrease in GH has been associated with a decrease in bone density and an increase in intra-abdominal fat.

Pharmaceutical GH therapy is being offered but is not appropriate for healthy people. The nutritional supplements currently being offered contain various secretagogue amino acids for increasing GH levels. Although secretagogue amino acids are known to assist in stimulating hormones that promote GH secretion, they are believed to not successfully block inhibitors of GH secretion. Accordingly, there remains a need for compositions and methods that have improved efficacy in increasing GH levels in mammals.

In this regard, it has now been found that acetylcholinesterase inhibitors, namely huperzine A, in combination with secretatgogue amino acids are useful in treating age-associated diseases by increasing GH levels to young adult levels. Accordingly, compositions containing effective amounts of huperzine A and secretagogue amino acids and methods thereof are desired.

SUMMARY OF THE INVENTION

A neutraceutical composition is provided for increasing GH levels in a mammal and includes effective amounts of huperzine A and secretagogue amino acids. The composition may further include a neutraceutically acceptable carrier or diluent. In a second aspect of the present invention, a method of increasing GH levels in a mammal and includes administering to the mammal an effective amount of huperzine A and secretagogue amino acids. In this regard, the present invention contemplates methods and compositions for increasing GH levels in a mammal and thereby treating age-associated diseases. These and other aspects and advantages of the present invention will be better understood by reference to the drawings and the detailed description of the preferred embodiment.

DETAILED DESCRIPTION OF THE INVENTION

Figure 1:
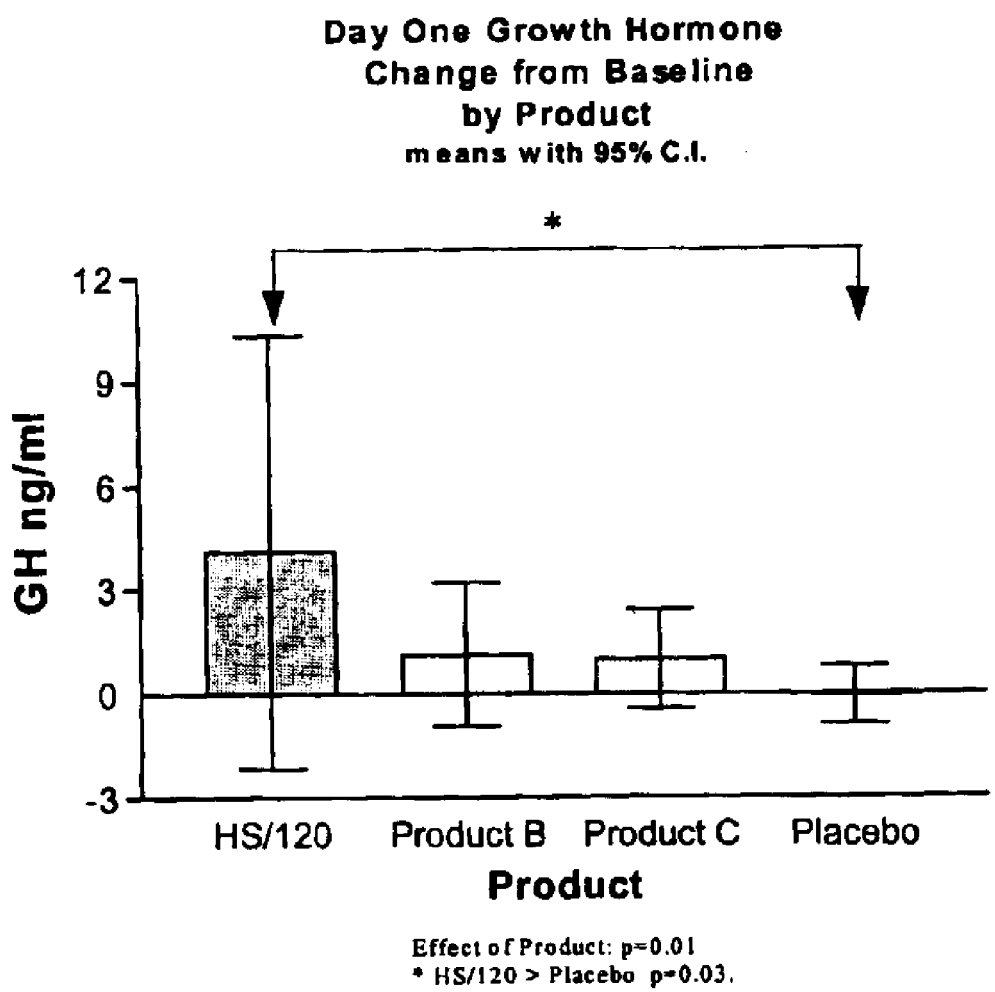
FIG. 1 shows the mean rise of GH in a human subject after consumption of the composition prepared in accordance with the present invention.

The present invention includes compositions containing acetylcholinesterase inhibitors and secretagogue amino acids for increasing GH levels in a mammal and methods thereof. In one aspect of the present invention a composition for increasing GH levels in a mammal is provided. A desired composition includes effective amounts of huperzine A, glycine and L-glutamine. Effective amounts of huperzine A, glycine, and L-glutamine will depend on the desired effect on GH levels. Desirably, the effective amount of huperzine A, glycine, and L-glutamine may include an amount able to increase GH levels by about 3 ng/ml above baseline levels. A daily dosage may include about 150 mcg of huperzine A, about 5.6 g glycine, and about 2 g L-glutamine. The presence of both huperzine A and secretagogue amino acids provides and effective increase in GH levels in mammals.

In another aspect of the present invention, a method for increasing GH levels in a mammal is provided. A desired method includes administering to a human subject an effective amount of huperzine A, glycine, and L-glutamine. The composition can be administered as needed to increase GH levels. Effective amounts of the composition may be administered approximately every 2 hours as desired to increase GH levels or administered daily for at least about 3 months.

Huperzine A for the present invention can be extracted from Chinese club moss, *Huperzia serrata*, or can be chemically synthesized by known means in the art. Huperzine A inhibits acetylcholinesterase which, in turn, inhibits acetylcholine. Acetylcholine is an enzyme that stimulates the secretion of GH from the pituitary gland. Other acetylcholinesterase inhibitors may be combined with or substituted in place of huperzine A in the present invention. These inhibitors may include huperzine B.

Secretagogue amino acids stimulate the growth hormone releasing hormone, sermorelin, which stimulates GH production and release. Other secretagogue amino acids may be used in place of or in combination with L-glutamine and glycine. Secretatgogue amino acids useful in the present invention may include: L-ornithine L-arginine, L-tryptophan, and L-carnitine.

It is contemplated that the combination of an acetylcholinesterase inhibitor and secretagogue amino acids may provide a synergistic effect on GH not present when secretagogue amino acids or acetylcholinesterase inhibitors are administered separately. It is also contemplated that the composition of the present invention may also increase IGF-1 and IGFBP-3. GH does not last long in our bloodstream as the liver absorbs GH and converts it into growth factors. IGF-1, also known as somatomedin-C, is a hormone like GH and an important growth factor that is produced. IGFBP-3 is also important because it promotes apoptosis or programmed cell death and, as such, may be necessary to protect from the potentially carcinogenic effects of GH and IGF-1.

The present composition may be administered in any manner suitable to provide an effective amount to a mammal. Accordingly, all oral dosage forms are contemplated for use in accordance with the present invention. Representative oral dosage forms include but are not limited to pills, capsules, gel caps, gel tabs, beverages, powdered beverage mixes, chewing gum, chewable tablets, lozenges, viscous gels, toothpastes, dental implants, mouth rinses and the like.

The composition may take the form of, for example, tablets or capsules prepared by conventional means with neutraceutically acceptable diluents, carriers, or excipients such as binding agents (e.g. pregelatinized maize starch, polyvinyl pyrrolidone or hydroxypropyl methylcellulose); fillers (e.g. lactose, microcrystalline cellulose or calcium hydrogen phosphate); lubricants (e.g. magnesium stearate, talc, or silica); disintegrants (e.g. potato starch or sodium starch glycolate); or wetting agents (e.g. sodium lauryl sulfate). The tablet may be coated by methods well known in the art. The composition may optionally include sweeteners, preservatives, vitamins, and minerals.

The compositions for oral administration may also be formulated to give controlled release of the active compounds. The active compounds of the present invention may be formulated as controlled release powders of discrete micro-particles that can be readily formulated in liquid form. The sustained release powder comprises particles containing an active ingredient and, optionally, an excipient with at least one non-toxic polymer. The powder can be dispersed or suspended in a liquid vehicle and will maintain its sustained release characteristics for a useful period of time. These dispersions or suspensions have both chemical stability and stability in terms of dissolution rate. The powder may contain excipients comprising a polymer, which may be soluble, insoluble, permeable, impermeable, or biodegradable. The polymers may be polymers or copolymers. The polymer may be a natural or a synthetic polymer.

The following example illustrates the effect of the present composition in GH levels, but does not limit the present invention.

EXAMPLE

A double-blind, placebo-controlled study was conducted comparing the effects of the following three beverage products on the stimulation of GH in healthy adults: a 450 ml beverage according to the present invention ("HS/120"); a commercial prototype ("Product B"), a commercially available product ("Product C"); and a placebo. The materials and amounts tested are as follows:

| HC/120 | |
|---|---|
| Active Ingredients in one 450 ml beverage | |
| Huperzine A | 150 mcg |
| Glycine | 5600 mg |
| L-glutamine | 2000 mg |

| Product B | |
|---|---|
| Arginine pyroglutamate | 2 g |
| Ornithine alpha-keto glutarate | 2 g |
| L-lysine | 2 g |
| L-glutamine | 2 g |
| Tyrosine | 2 g |
| Bovine colustrum (15% IgG) | 2 g |
| American ginseng root extract (5% ginsenosides) | 200 mg |
| Macuna pruriens (10% L-dopa, 20% total catecholamines) | 25 mg |
| Vitamin B-6 (as pyridoxine hcl) | 10 mg |
| Co enzyme Q-10 | 5 mg |

| Product C | |
|---|---|
| Vitamin B12 | 1 mg |
| Calcium | 224 mg |
| Iron | 4 mg |
| Phosporus | 364 mg |
| Magnesium | 39 mg |
| Zinc | 1.06 mg |
| Selenium | 8 mcg |
| Copper | 0.23 mg |
| Manganese | 0.4 mg |
| Sodium | 805 mg |
| Potassium | 288 mg |
| L-Isoleucine | 1399 mg |
| L-Leucine | 2448 mg |
| L-Lysine | 1098 mg |
| L-Methionine | 350 mg |
| L-Phenylalanine | 1400 mg |
| L-Threonine | 1400 mg |
| L-Alanine | 1400 mg |
| L-Arginine | 2098 mg |
| L-Aspartic Acid | 3147 mg |
| L-Cystine | 350 mg |
| L-Glutamic Acid | 5595 mg |
| Glycine | 1049 mg |
| L-Proline | 1748 mg |
| L-Serine | 1748 mg |
| L-tyrosine | 1049 mg |

Six subjects, 4 women and 2 men, participated in this double-blind, placebo-controlled, fully randomized study. Each subject drank one beverage a day each morning, four days a week for four weeks. Every new study week the beverage was changed for each subject, such that in four weeks all subjects consumed four single, consecutive daily doses of each product and the placebo product. All products were consumed after a 10-hour overnight fast.

Blood was drawn before as well as 30, 60, 90, 120 and 180 minutes after the consumption of each product on Day 1 and Day 4. FIG. 1 shows that the present invention, HS/120, caused a mean rise of 4.1 ng/ml of GH above placebo response and above baseline on Day 1. HS/120 is associated with a greater mean peak GH rise above baseline than placebo on Day 1 than all other products. The mean peak GH rises above baseline associated with the other products were not significantly higher than that associated with placebo response. The data on peak rise above baseline was analyzed with Friedman's test, which revealed a significant effect of product, $p=0.01$. Dunn's Multiple Comparisons (corrected p values) revealed that HS/120 showed significantly higher GH peaks above baseline than placebo, $p=0.03$. No other product attained a similar rise.

Figure 2A:
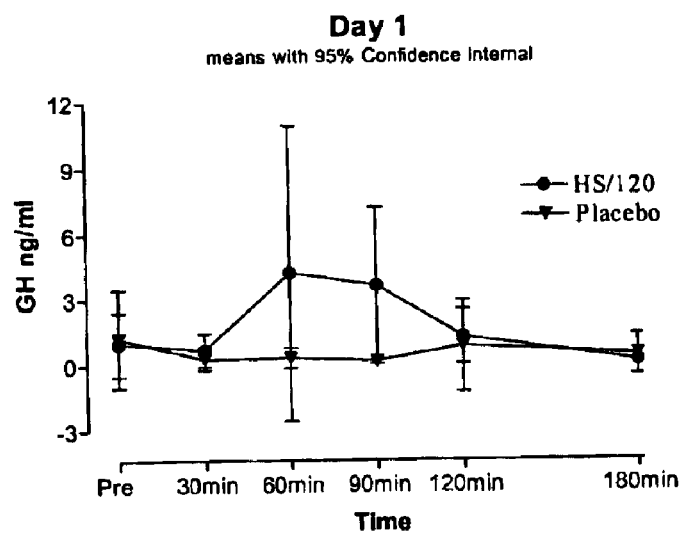
FIGS. 2A–2B show the GH response curve of the composition of the present invention in comparison to a placebo over certain time intervals.
Figure 2B:
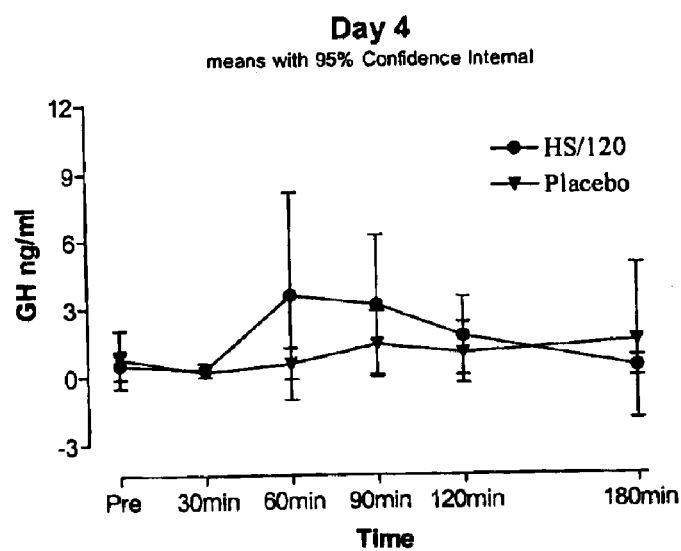

Although the main outcome measure was a peak rise above baseline at any time within three hours of consumption of an active product (as illustrated in FIG. 1), the response curves over time for each product and testing day was also examined. FIGS. 2a and 2b show that HS/120 is associated with a GH response beginning between 30–60 min after consumption and lasting at most 90 min.

While the above describes what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed:

1. A method of increasing GH levels comprising administering to a mammal a composition wherein the composition includes about 150 mcg of huperzine A, about 5.6 g glycine, and about 2 g L-glutamine and wherein the composition increases GH levels to about 3 ng/ml in about 30 minutes to about 90 minutes after administration.

2. The method of claim 1 wherein the composition is a beverage.

3. The method of claim 1 wherein the composition is a nutritional supplement.

4. The method of claim 1 wherein the composition increases GH levels in about 30 minutes to about 60 minutes.

* * * * *